United States Patent
Kang et al.

(10) Patent No.: US 10,203,312 B2
(45) Date of Patent: Feb. 12, 2019

(54) SYSTEM FOR MEASURING CARBON EMISSION IN POWER SYSTEM

(71) Applicant: Tsinghua University, Beijing (CN)

(72) Inventors: Chongqing Kang, Beijing (CN); Yaohua Cheng, Beijing (CN); Ning Zhang, Beijing (CN); Qixin Chen, Beijing (CN); Qing Xia, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 58 days.

(21) Appl. No.: 15/459,059

(22) Filed: Mar. 15, 2017

(65) Prior Publication Data

US 2018/0067089 A1 Mar. 8, 2018

(30) Foreign Application Priority Data

Sep. 6, 2016 (CN) .......................... 2016 1 0805076

(51) Int. Cl.
*G01N 33/00* (2006.01)
*G06Q 10/06* (2012.01)
*G06Q 50/06* (2012.01)

(52) U.S. Cl.
CPC ....... *G01N 33/004* (2013.01); *G01N 33/0062* (2013.01); *G06Q 10/06* (2013.01); *G06Q 50/06* (2013.01); *Y02E 40/76* (2013.01); *Y02P 90/82* (2015.11); *Y02P 90/84* (2015.11); *Y04S 10/545* (2013.01)

(58) Field of Classification Search
CPC ... G01N 33/0062; G01N 33/004; G06Q 10/06
See application file for complete search history.

(56) References Cited

U.S. PATENT DOCUMENTS

| | | | |
|---|---|---|---|
| 2010/0287012 A1 | 11/2010 | Ballantine et al. | |
| 2013/0204452 A1 | 8/2013 | Yamaguchi et al. | |
| 2016/0019084 A1* | 1/2016 | Forestiero | G06F 9/5088 718/1 |
| 2018/0031533 A1* | 2/2018 | Rawat | G06Q 50/06 |

FOREIGN PATENT DOCUMENTS

CN 103218690 7/2013

OTHER PUBLICATIONS

EPO, Office Action for EP Application No. 17158930, dated Jul. 4, 2017.

* cited by examiner

*Primary Examiner* — Bryan Bui
(74) *Attorney, Agent, or Firm* — Hodgson Russ LLP

(57) ABSTRACT

The present disclosure provides a system for measuring carbon emissions in a power system. The system includes: generation carbon meters, distributed respectively in generators in the power system; network carbon meters, distributed respectively in nodes in the power system; consumption carbon meters, distributed respectively in consumers in the power system; and a center server, in which each carbon meter is configured to collect data for measuring the carbon emissions. The center server is configured to acquire the collected data and to measure the carbon emissions according to the acquired data, and to send measuring results to the corresponding carbon meter. Then each carbon meter is further configured to display according to the measuring results. The carbon emission may be measured in real time.

11 Claims, 3 Drawing Sheets

SYSTEM FOR MEASURING CARBON EMISSION IN POWER SYSTEM

CROSS-REFERENCE TO RELATED APPLICATIONS

This application is based upon and claims a priority to Chinese Patent Application Serial No. 201610805076.0, filed with the State Intellectual Property Office of P. R. China on Sep. 6, 2016, the entire contents of which are incorporated herein by reference.

Field

The present disclosure generally relates to field of low-carbon technology of a power system, and more particularly, to a system for measuring carbon emissions in a power system.

Background

The energy crisis and global climate change are fallen under observation increasingly. Reducing excessive consumption of fossil fuel and realizing a low-carbon development have been common goals around the world. A power system, as an essential part of energy supply, is a main source of fossil fuel consumption, thereby generating a large amount of carbon emissions. Therefore, reducing the carbon emission amount in the power system and constructing a low-carbon power system are important to achieve low-carbon development.

In the related art, a measurement of the carbon emission is mainly based on macro data and statistic data, which neglects network features of the power system. Therefore, it cannot measure the carbon emission in real time and display the carbon emission caused by consumers directly.

SUMMARY

A system for measuring carbon emissions in a power system is provided in embodiments of the present disclosure. The system includes: generation carbon meters, distributed respectively in generators in the power system; network carbon meters, distributed respectively in nodes in the power system; consumption carbon meters, distributed respectively in consumers in the power system; and a center server, in which each carbon meter is configured to collect data for measuring the carbon emissions, the center server is configured to acquire the collected data and to measure the carbon emissions according to the acquired data and to send measuring results to the corresponding carbon meter, and each carbon meter is further configured to display the measuring results.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

The above and/or additional aspects and advantages of embodiments of the present disclosure will become apparent and more readily appreciated from the following descriptions made with reference to the drawings, in which.

DETAILED DESCRIPTION

Referring to the following descriptions and drawings, these and other aspects of the embodiments of the present disclosure will be apparent. In these descriptions and drawings, some specific approaches of the embodiments of the present disclosure are provided, so as to show some ways to perform the principle of the embodiments of the present disclosure, however it should be understood that the embodiment of the present disclosure is not limited thereby. Instead, the embodiments of the present disclosure include all the variants, modifications and their equivalents within the spirit and scope of the present disclosure as defined by the claims.

A system for measuring carbon emissions in a power system may be provided in the embodiments of the present disclosure, which will be described as follows.

The carbon emission flow can be acquired in the embodiments of the present disclosure, which depends on a power flow distribution and carbon emission embedded with active power flow directional movement. There are some indicators of the carbon emission flow.

(1) A nodal carbon emission flow intensity: the carbon emission amount associated with a unit of power flow that is injected into the node, which is in $kgCO_2/kWh$.

(2) A carbon emission flow rate (CEFR for short): the quantity of carbon emission flow that flowing through a node or a branch during a unit of time. The unit is $kgCO_2/s$ (second) or $tCO_2/s$. There are three types of CEFR, CEFR of the node (NCEFR for short), CEFR of the branch (BCER for short) and a CEFR incurred by transmission loss of a branch (BCEL for short).

(3) A carbon emission flow amount: a basic physical quantity depicting the quantity of carbon emission flow, which is an accumulated carbon emission amount embedded with the power flow during a given period and is in $kgCO_2$ or in $tCO_2$.

(4) A carbon emission flow intensity of the branch: an amount of carbon emission flow associated with a unit of active power flow along a given branch, which is used to characterize the relationship between carbon emission flow and the power flow and in $kgCO_2/kWh$.

(5) A carbon emission intensity of a generator: a carbon emission amount caused by generating a unit of electric energy via a generator, which is in $kgCO_2/kWh$.

For a thermal power generator, the carbon emission intensity of the generator is acquired by real-time fossil fuel consumption and the operating state; for other generator, such as a hydropower generator, a wind power generator, a photovoltaic generator or a like, the carbon emission intensity of the generator is 0.

Figure 1:
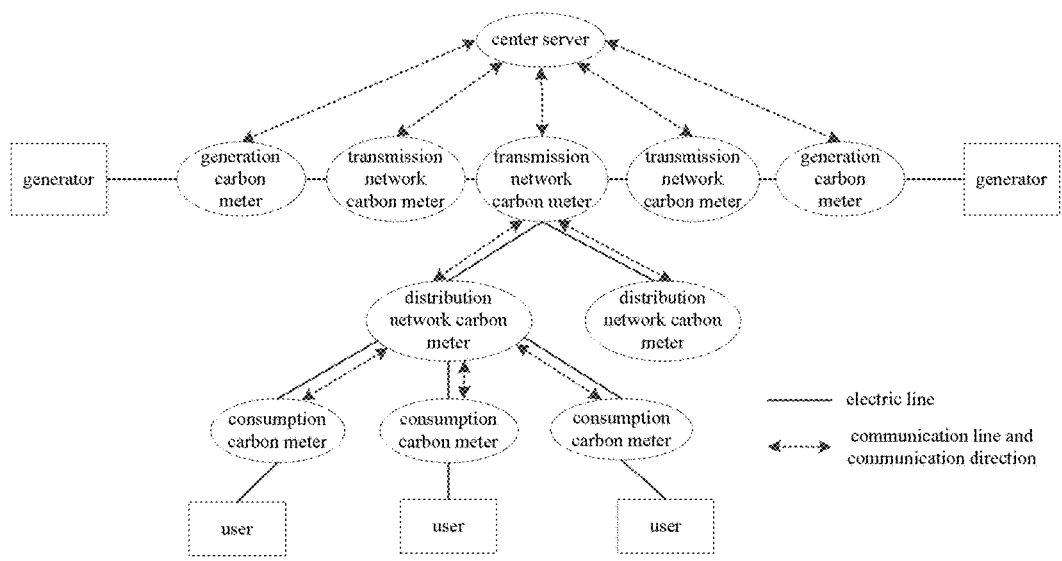
FIG. 1 is a schematic diagram illustrating a system for measuring carbon emissions in a power system according to an embodiment.

FIG. 1 is a schematic diagram illustrating a system for measuring carbon emissions in a power system according to an embodiment. As shown in FIG. 1, the system includes: generation carbon meters, network carbon meters, consumption carbon meters and a center server. Further, in an embodiment of the present disclosure, the network carbon meters include transmission network carbon meters and distribution network carbon meters.

The generation carbon meters are distributed respectively in generators in the power system. The network carbon meters are distributed respectively in nodes in the power system. The consumption carbon meters are distributed respectively in consumers in the power system.

In an embodiment of the present disclosure, each carbon meter is configured to collect data for measuring the carbon emissions, the center server is configured to acquire the collected data and to measure the carbon emissions according to the acquired data and to send measuring results to the corresponding carbon meter, and each carbon meter is further configured to display according to the measuring results.

In an embodiment of the present disclosure, each generation carbon meter is configured to acquire a carbon emission intensity of the corresponding generator; the center server is configured to receive the carbon emission intensities of the generators to acquire a carbon emission intensity vector of the generators; receive injection active power of the generators; generate a power injection distribution matrix of the generators according to the injection active power of the generators and topological structure information of the power system; acquire a branch power outflow distribution matrix and a nodal active power flow flux matrix according to power flow and the topological structure information of the power system; and acquire carbon emission flow results according to the branch power outflow distribution matrix, the power injection distribution matrix, the nodal active power flow flux matrix and the carbon emission intensity vector, in which the carbon emission flow includes at least one of nodal carbon emission flow intensities, carbon emission flow rates of the branches, and carbon emission flow rates of loads.

Figure 2:
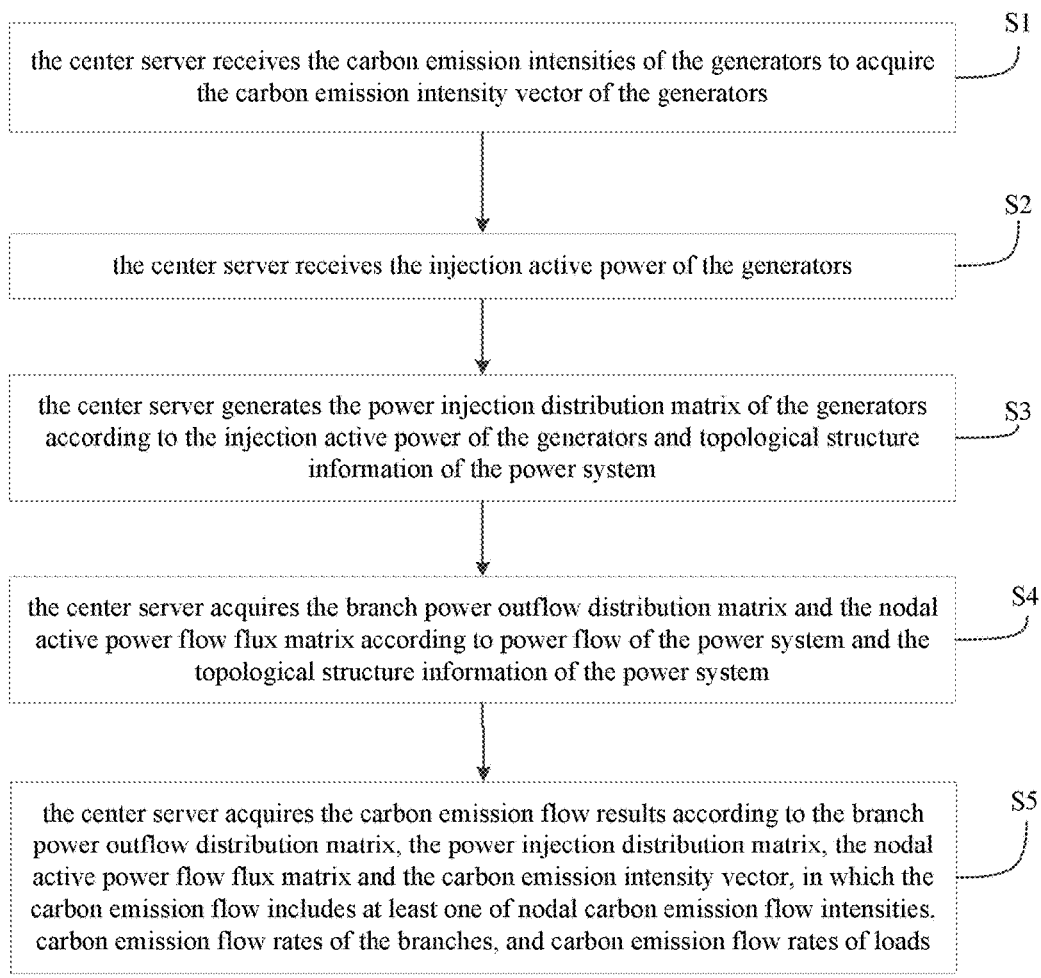
FIG. 2 is a flow chart of acquiring a carbon emission flow by a center server according to an embodiment.

This process of acquiring the carbon emission flow by the center server can be shown in FIG. 2 and described as follows.

At step S1, the center server receives the carbon emission intensities of the generators to acquire the carbon emission intensity vector of the generators.

In an embodiment, the carbon emission intensity of the generator is varied with the types of the generators, which is acquired from each generation carbon meter. If the carbon emission intensity of a $k^{th}$ generator is denoted by $e_{Gk}$, the carbon emission intensity vector of the generators is denoted by $$E_G = [e_{G1}, e_{G2}, \ldots, e_{GK}]^T$$

where, k=1, 2, . . . K, K denotes the number of the generators.

At step S2, the center server receives the injection active power of the generators.

At step S3, the center server generates the power injection distribution matrix of the generators according to the injection active power of the generators and topological structure information of the power system.

In an embodiment, an element of the power injection distribution matrix of the generators is denoted by that: $P_{Gkj}=p$, if the $k^{th}$ generator joins up a node j and an active power flow p is injected into the node; or $P_{Gkj}=0$, otherwise; where, $P_{Gkj}$ denotes the element in the power injection distribution matrix $P_G$ and k is a positive integer.

The power injection distribution matrix describes connection relationships of all generators and the power system as well as the active powers injected into the power system by the generators. The power injection distribution matrix also describes boundary conditions for generating the carbon emission flow by the generators in the power system.

At step S4, the center server acquires the branch power outflow distribution matrix and the nodal active power flow flux matrix according to power flow of the power system and the topological structure information of the power system.

In an embodiment, an element of the branch power outflow distribution matrix is denoted by that: $P_{Bij}=0$ and $P_{Bji}=p$, if a node i connects with a node j via a branch and an active power flow p is flowed into the node i via the branch, or $P_{Bij}=p$ and $P_{Bji}=0$, if a node i connects with a node j via a branch and an active power flow p is flowed out from the node i via the branch, or $P_{Bij}=P_{Bji}=0$, if a node i does not connect with a node j; and $P_{Bii}=0$; where, i and j are positive integers respectively, i is not equal to j $P_{Bij}$ denotes the element in the branch power outflow distribution matrix $P_B$ at an intersection between an $i^{th}$ row and a $j^{th}$ column, and $P_{Bji}$ denotes the element in the branch power outflow distribution matrix $P_B$ at an intersection between at $j^{th}$ row and an $i^{th}$ column.

The branch power outflow distribution matrix describes distribution of active power flow in the power system. This matrix includes the topological structure information of the power system and the distribution information of active power flow in the power system in steady-state.

In an embodiment, an element of the nodal active power flow flux matrix is denoted by a formula of:

$$\begin{cases} P_{Nii} = \sum_{s \in I^+} p_{Bs} + P_{Gi} \\ P_{Nij} = 0, i \neq j \end{cases}$$

where, $I^+$ denotes a set of branches via which a power is injected into a node i, $p_{Bs}$ denotes an active power of a branch s, $P_{Nii}$ denotes the element in the nodal active power flow flux matrix $P_N$ at an $i^{th}$ row and an $i^{th}$ column, $P_{Nij}$ denotes the element in the nodal active power flow flux matrix $P_N$ at the $i^{th}$ row and an $i^{th}$ column, and $P_{Gi}$ denotes an active output of a generator joining up the node i, $P_{Gi}$ is equal to 0 if there is no generator at the node i.

In the calculation of the carbon emission flow, the nodal carbon emission flow intensity is only affected by injection flow, and is not affected by flow output from the node; therefore, the calculation of the carbon emission flow only focus on considering an absolute value of the active power flow injected into the node.

At step S5, the center server acquires the carbon emission flow results according to the branch power outflow distribution matrix, the power injection distribution matrix, the nodal active power flow flux matrix and the carbon emission intensity vector, in which the carbon emission flow includes at least one of nodal carbon emission flow intensities, carbon emission flow rates of the branches, and carbon emission flow rates of loads.

In an embodiment, the nodal carbon emission flow intensities are acquired by a formula of:

$$E_N = (P_N - P_B^T)^{-1} \cdot P_G^T \cdot E_G$$

where, $E_N$ is a vector denoting the nodal carbon emission flow intensities, $P_N$ denotes the nodal active power flow flux matrix, $P_B$ denotes the branch power outflow distribution matrix, $P_G$ denotes the power injection distribution matrix and $E_G$ denotes the carbon emission intensity vector.

In an embodiment, an element in the vector $E_N$ is denoted by a formula of:

$$e_{Ni} = \frac{\sum_{s \in I^+} P_{Bs} \cdot \rho_s + P_{Gi} \cdot e_{Gi}}{\sum_{s \in I^+} P_{Bs} + P_{Gi}}$$

where, $I^+$ denotes a set of branches via which a power is injected into a node i, $P_{Bs}$ denotes an active power of a branch s, $P_{Gi}$ denotes an active power injected by a generator joining up the node i, $\rho_s$ denotes a carbon emission flow density of the branch s, and $e_{Gi}$ denotes a carbon emission intensity of the generator joining up the node i.

In an embodiment, the carbon emission flow rate of the branch is denoted by a formula of:

$$R_{BL} = P_{BL} \cdot e_N$$

where, $R_{BL}$ denotes the carbon emission flow rate of the branch, $P_{BL}$ denotes an active power flow of the branch and $e_N$ denotes a nodal carbon emission flow intensity of a start node.

In an embodiment, the carbon emission flow rate of the load is denoted by a formula of:

$$R_{BD} = P_{BD} \cdot e_N$$

where, $R_{BD}$ denotes the carbon emission flow rate of the load, $P_{BD}$ denotes an active power of the load, and $e_N$ denotes a nodal carbon emission flow intensity of a node at which a load is located.

In an embodiment of the present disclosure, as shown in FIG. 1, the transmission network carbon meters are distributed respectively in transmission network of the power system and the distribution network carbon meters are distributed respectively in distribution network of the power system.

As shown in FIG. 1, the system is divided into three levels. A lower level includes the consumption carbon meters, a middle level includes the distribution network carbon meters, and an upper level includes the center server, the generation carbon meters and the transmission network carbon meters.

The center server is configured to communicate with each generation carbon meter and each transmission network carbon meter, and to send the carbon emission flow results to each transmission network carbon meter, and each transmission network carbon meter is further configured to display the carbon emission flow results in real-time.

Each distribution network carbon meter is configured to communicate with the corresponding transmission network carbon meter and to obtain the nodal carbon emission flow intensity corresponding to a root node connecting the distribution network and the transmission network, and to acquire a carbon emission flow results of the corresponding distribution network based on the nodal carbon emission flow intensity of the root node and the power flow of the distribution network.

The carbon meters are distributed at positions where carbon emissions need to be measured. The center server is taken as a calculating center configured to acquire the carbon emission flow results and configured to communicate with the power meters to acquire a power flow distribution of the power system. The carbon meters include four kinds of carbon meters (the generation carbon meters, the transmission network carbon meters, the distribution network carbon meters, and the consumption carbon meters). The generation carbon meter is installed at a position in a generator. The transmission network carbon meter or the distribution network carbon meter is respectively installed at each node of the transmission network and distribution network of the power system. The consumption carbon meter is installed at a position in a consumption side. The carbon meters are configured to collect data for calculating the carbon emission flow, to communicate the collected data with the center server via the communication lines and to display the carbon emission flow results fed back by the center server. The system is divided into 3 levels according to a communication structure. A solid line represents an electric line and a dotted line with arrows represents a communication line and a communication direction.

In an embodiment, the center server is configured to measure and display the carbon emission in real time by communicating with the carbon meters, in connection with a data collection and display function of the carbon meters. Parameters measured and displayed by the carbon meters include the nodal carbon emission flow intensities, real-time carbon emission amounts and accumulated carbon emission amounts. For the consumption carbon meter, data, such as an electric power, an accumulated electric energy and the like, further needs to be displayed, in which the data is acquired by communicating with the center server. In addition to acquiring the above parameters, there are different functions corresponding to the carbon meters. Detailed descriptions are made below.

The generation carbon meter is installed in an exit of the generator of the power system and is further configured to measure the carbon emission intensity of the corresponding generator in the system power and to acquire the carbon emission intensity of the corresponding generator according to real-time data of the generator and to communicate associated information with the center server.

For a thermal power generator, the carbon emission intensity of the corresponding generator is acquired in real-time by a formula:

$$e_G = 7 \cdot r \cdot \frac{EF_M}{q}$$

In an embodiment, $e_G$ is in $kgCO_2/kWh$, r is the standard coal consumption rate for generating of thermal power generator and is in gce/kWh, $EF_M$ is the carbon emission coefficient of the thermal power generator and is in kg $CO_2$/kg, and q is heat combustion of the thermal power generator and is in kcal/kg (Kilo calorie/kg).

For those generators with renewable energy resources, such as a hydropower generator, a wind power generator, a photovoltaic generator or a like, the carbon emission intensity is 0.

In an embodiment, the generation carbon meter is further configured to acquire a real-time carbon emission amount of the generator and an accumulated carbon emission amount of the generator. The real-time carbon emission amount of the generator is denoted by a formula of:

$$E_{Gt} = P_G \cdot \Delta t \cdot e_{Gt};$$

and the accumulated carbon emission amount of the generator is denoted by a formula of:

$$E_G = \sum_{t \in T} P_{Gt} \cdot \Delta t \cdot e_{Gt},$$

where, $E_{Gt}$ denotes the carbon emission amount of the generator G during a period t, $E_G$ denotes the accumulated carbon emission amount of the generator G during the period t, $P_{Gt}$ denotes an active power output of the generator G during the period t, $\Delta t$ denotes a duration of the period t, $e_{Gt}$ denotes the carbon emission intensity of the generator G during the period t and T denotes a set of periods t.

In an embodiment, the transmission network carbon meter or the distribution network carbon meter is further configured to acquire a real-time carbon emission amount of a power loss of a branch connecting with a node or to acquire a real-time carbon emission amount of a power loss of a transformer connecting with a node; and to acquire an accumulated carbon emission amount of a power loss of a branch connecting with a node or to acquire an accumulated carbon emission amount of a power loss of a transformer connecting with a node. The real-time carbon emission amount of the power loss of the branch connecting with the node or the real-time carbon emission amount of the power loss of the transformer connecting with the node is denoted by a formula of:

$$E_{Nt} = (P_{1t} - P_{2t}) \cdot \Delta t \cdot e_{Nt}; \text{ and}$$

the accumulated carbon emission amount of the power loss of the branch connecting with the node or the accumulated carbon emission amount of the power loss of the transformer connecting with the node is denoted by a formula of:

$$E_N = \sum_{t \in T} (P_{1t} - P_{2t}) \cdot \Delta t \cdot e_{Nt},$$

where, $E_{Nt}$ denotes the carbon emission amount of the branch connecting with the node or the transformer connecting with the node, $E_N$ denotes the accumulated carbon emission amount of the branch connecting with the node or the transformer connecting with the node, $P_{1t}$ denotes an active power of a start node of the branch during a period t or an active power of a primary side of the transformer during a period t, $P_{2t}$ denotes an active power of an end node of the branch during the period t or an active power of a secondary side of the transformer during the period t, $e_{Nt}$ denotes a nodal carbon emission flow intensity of the start node of the branch or a carbon emission intensity of the primary side of the transformer, $e_{Nt}$ is acquired from the center server, $\Delta t$ denotes a duration of the period t, and T denotes a set of periods t.

In an embodiment, the consumption carbon meter is further configured to acquire a real-time carbon emission amount of a consumer and an accumulated carbon emission amount of a consumer. The real-time carbon emission amount of the consumer is denoted by a formula of:

$$E_{Ct} = P_{Ct} \cdot \Delta t \cdot e_{Ct}; \text{ and}$$

the accumulated carbon emission amount of the consumer is denoted by a formula of:

$$E_C = \sum_{t \in T} P_{Ct} \cdot \Delta t \cdot e_{Ct},$$

where, $E_{Ct}$ denotes the carbon emission amount of the consumer $E_C$ denotes the accumulated carbon emission amount of the consumer, $P_{Ct}$ denotes an active power of loads corresponding to the consumer during the period t, $e_{Ct}$ denotes a nodal carbon emission flow intensity of a node at which the consumer located and is acquired from the carbon emission flow of the corresponding distribution network, $\Delta t$ denotes a duration of the period t, and T denotes a set of periods t.

A specific working process of the system may be described as follows.

1) The upper level of the system is configured to acquire the carbon emission flow results in the power system.

The generation carbon meter acquires the carbon emission intensity corresponding to the generator, the carbon emission amount corresponding to the generator, and the accumulated carbon emission amount corresponding to the generator as above, by collecting data, and communicates the carbon emission intensity of the generator to the center server. Then, the center server acquires the carbon emission flow results according to the carbon emission intensities of the generators and a network power flow distribution self-acquired via the process provided in embodiments of the present disclosure.

The center server communicates with both the generation carbon meters and the transmission network carbon meters to calculate the nodal carbon emission flow intensities, the carbon emission flow rates and transmit results to the transmission network carbon meters. The transmission network carbon meter displays the nodal carbon emission flow intensity, the carbon emission flow rate and the active power communicated by the center server.

2) The middle level has the distribution network carbon meters. The distribution network carbon meter acquires the carbon emission intensity of the root node and an injection power of the root node by communicating with the transmission network carbon meter and acquires the carbon emission flow results of the distribution network. The called "root node" is a node connecting a power distribution network and a power transmission network.

As the distribution network is radial grid shaped, the nodal carbon emission flow intensity of the node in the distribution network is acquired by that, the nodal carbon emission intensity of each node in the distribution network is acquired along a radial direction from the root node and the nodal carbon emission intensity of the node at which a terminal load is located is finally acquired.

In an embodiment, the carbon emission intensity of the node in the distribution network is denoted by a formula of:

$$e_{Ni} = \frac{\sum_{s \in I^+} P_{Bs} \cdot \rho_s + P_{Ri} \cdot e_{Ri}}{\sum_{s \in I^+} P_{Bs} + P_{Ri}}$$

where, $I^+$ denotes a set of branches via which a power is injected into a node i, $P_{Bs}$ denotes an active power of a branch s, $\rho_s$ denotes a carbon emission flow intensity of the branch s, $P_{Ri}$ denotes an active power injected into the node i and $e_{Ri}$ denotes the nodal carbon emission intensity of the root node connecting with the node i.

After the carbon emission flow results is acquired by the distribution network, the real-time carbon emission amount of the consumer is acquired. Acquiring the real-time carbon emission amount of the consumer is realized by the lower level of the system.

3) The lower level has the consumption carbon meters. The consumption carbon meter communicates with the distribution network carbon meter to acquire the carbon emission intensity of the node at which the consumer is located. The carbon emission amount caused by the consumer is acquired as above.

With the system, the carbon emission in the power system is measured precisely in real time. Furthermore, the carbon emission flow distribution of the power system is measured and the results are directly displayed. Furthermore, the carbon emission intensity and carbon emission flow rate of the branches and the nodal carbon emission flow intensity of the node, in the power system are acquired.

After the above processes, the real-time carbon emission amount and the accumulated carbon emission amount of the generator and the power loss are acquired and displayed. Furthermore, the real-time carbon emission amount of the consumer and the accumulated carbon emission amount of the consumer are acquired and displayed.

In an example, the system may be applied into an IEEE 24 node system.

In an example, there are 12 generators in the IEEE 24 node system. The parameters of the generators are shown in Table 1.

TABLE 1

Parameters of generators

| No. of generators | No. of nodes | power capacity (MW) | carbon emission intensity (kg $CO_2$/kWh) |
|---|---|---|---|
| 1 | 1 | 20 | 0.65 |
| 2 | 1 | 152 | 0.94 |
| 3 | 2 | 20 | 0.65 |
| 4 | 2 | 152 | 0.94 |
| 5 | 7 | 240 | 0.61 |
| 6 | 13 | 285.3 | 0.61 |
| 7 | 15 | 60 | 0.65 |
| 8 | 15 | 155 | 0.87 |
| 9 | 16 | 155 | 0.87 |
| 10 | 18 | 400 | 0 |
| 11 | 21 | 400 | 0 |
| 12 | 23 | 570 | 0.83 |

Parameters of the load are shown in Table 2

TABLE 2

Parameters of the load

| No. of nodes | Power (MW) |
|---|---|
| 1 | 108 |
| 2 | 97 |
| 3 | 180 |
| 4 | 74 |
| 5 | 71 |
| 6 | 136 |
| 7 | 125 |
| 8 | 171 |
| 9 | 175 |
| 10 | 195 |
| 13 | 265 |
| 14 | 194 |
| 15 | 317 |
| 16 | 100 |
| 18 | 333 |
| 19 | 181 |
| 20 | 128 |

Figure 3:
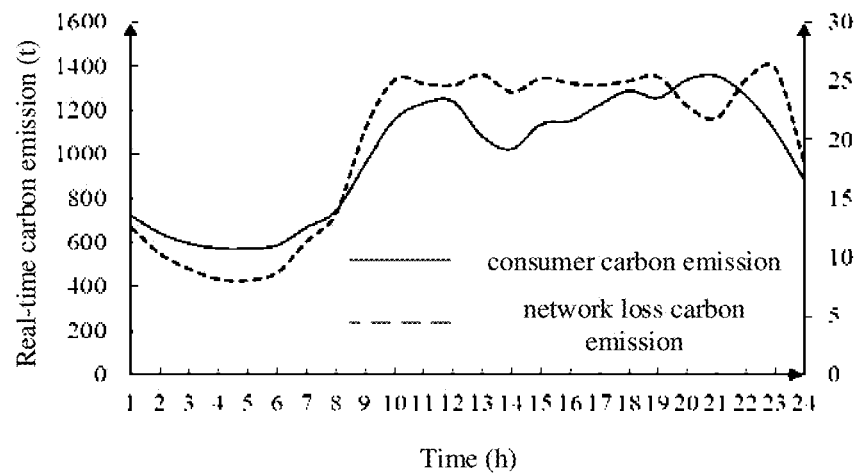
FIG. 3 is a schematic diagram illustrating real-time carbon emissions during each hour in daytime according to an embodiment.
Figure 4:
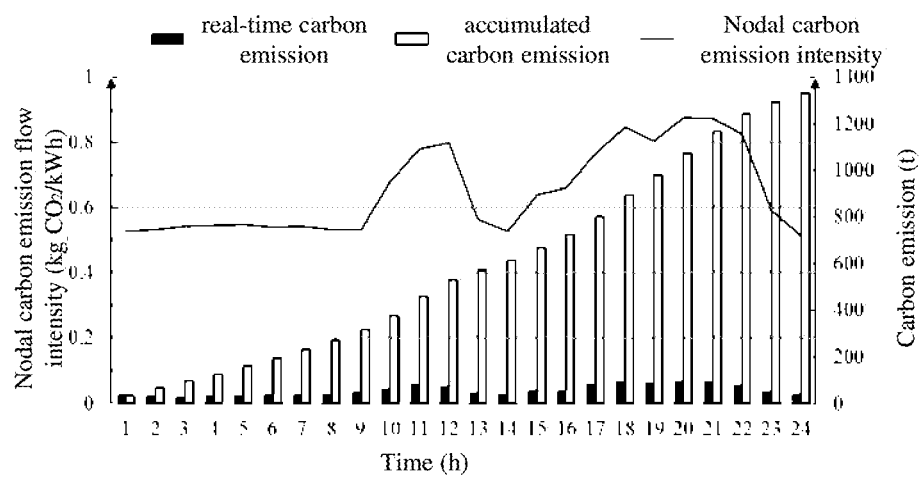
FIG. 4 is a schematic diagram illustrating a result of carbon emissions at node 1 according to an embodiment.

According to the system provided in embodiments of the present disclosure, a real-time carbon emission caused by a network loss and the consumer during each hour in daytime is shown in FIG. 3. A horizontal coordinate represents time in hour and a vertical coordinate represents a carbon emission amount in ton. In FIG. 3, consumer carbon emission represents the carbon emission caused by the consumer while network loss carbon emission represents the carbon emission caused by the network loss. Taking a node 1 as an example, the real-time carbon emission amounts, the accumulated carbon emission amounts and the nodal carbon emission flow intensities in the daytime are shown in FIG. 4. A horizontal coordinate represents time in hour, a main vertical coordinate represents the carbon emission intensity of the node in kg$CO_2$/kWh and a secondary vertical coordinate represents a carbon emission amount in t$CO_2$. In FIG. 4, bar charts represent the real-time carbon emission amount and the accumulated carbon emission amount while a curve represents a variation of the nodal carbon emission flow intensity of the node 1 over time.

In the description, terms such as "an embodiment," "some embodiments," "an example," "a specific example," or "some examples," means that a particular feature, structure, material, or characteristic described in connection with the embodiment or example is included in at least one embodiment or example of the present disclosure. Thus, the appearances of the above terms in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A system for measuring carbon emissions in a power system, comprising:
   generation carbon meters, distributed respectively in generators in the power system;
   network carbon meters, distributed respectively in nodes in the power system;
   consumption carbon meters, distributed respectively in consumers in the power system, wherein the network carbon meters comprise transmission network carbon meters and distribution network carbon meters, the transmission network carbon meters are distributed respectively in power transmission network of the power system and the distribution network carbon meters are distributed respectively in power distribution network of the power system; and
   a center server, wherein
   each carbon meter is configured to collect data for measuring the carbon emissions, the center server is configured to acquire the collected data and to measure the carbon emissions according to the acquired data and to send measuring results to the corresponding carbon meter, and each carbon meter is further configured to display according to the measuring results;
   the system is divided into three levels, a lower level comprises the consumption carbon meters, a middle level comprises the distribution network carbon meters, and an upper level comprises the center server, the generation carbon meters and the transmission network carbon meters,
   each generation carbon meter is configured to acquire a carbon emission intensity of the corresponding generator; and the center server is configured to:
  receive the carbon emission intensities of the generators to acquire a carbon emission intensity vector of the generators;
  receive injection active power of the generators;
  generate a power injection distribution matrix of the generators according to the injection active power of the generators and topological structure information of the power system;
  acquire a branch power outflow distribution matrix and a nodal active power flow flux matrix according to power flow and the topological structure information of the power system;
  acquire carbon emission flow results according to the branch power outflow distribution matrix, the power injection distribution matrix, the nodal active power flow flux matrix and the carbon emission intensity vector, wherein the carbon emission flow comprises at least one of nodal carbon emission flow intensities, carbon emission flow rates of the branches, and carbon emission flow rates of loads.

2. The system according to claim 1, wherein the center server is configured to communicate with each generation carbon meter and each transmission network carbon meter, and to send the carbon emission flow results to each transmission network carbon meter, and each transmission network carbon meter is further configured to display the carbon emission flow results in real-time.

3. The system according to claim 2, wherein each distribution network carbon meter is configured to communicate with the corresponding transmission network carbon meter and to obtain the nodal carbon emission flow intensity corresponding to a root node connecting the distribution network and the transmission network, and to acquire a carbon emission flow results of the corresponding distribution network based on the nodal carbon emission flow intensity corresponding to the root node.

4. The system according to claim 3, wherein each consumption carbon meter is configured to acquire a carbon emission amount of a consumer by a formula of:

$$E_{Ct}=P_{Ct} \cdot \Delta t \cdot e_{Ct};$$

and to acquire an accumulated carbon emission amount of the consumer by a formula of:

$$E_C = \sum_{t \in T} P_{Ct} \cdot \Delta t \cdot e_{Ct}$$

where, $E_{Ct}$ denotes the carbon emission amount of the consumer, $E_C$ denotes the accumulated carbon emission amount of the consumer, $P_{Ct}$ denotes an active power of loads corresponding to the consumer during the period t, $e_{Ct}$ denotes a nodal carbon emission intensity of a node at which the consumer located and is acquired from the carbon emission flow of the corresponding distribution network, $\Delta t$ denotes a duration of the period t, and T denotes a set of periods t;
  each consumption carbon meter is further configured to display the acquired carbon emission amount and the acquired accumulated carbon emission amount in real-time.

5. The system according to claim 1, wherein an element of the branch power outflow distribution matrix is denoted by that:

$P_{Bij}=0$ and $P_{Bji}=p$, if a node i connects with a node j via a branch and an active power flow p is flowed into the node i via the branch, or $P_{Bij}=p$ and $P_{Bji}=0$, if a node i connects with a node j via a branch and an active power flow p is flowed out from the node i via the branch, or $P_{Bij}=P_{Bji}=0$, if a node i does not connect with a node j; and $P_{Bii}=0$;

where, i and j are positive integers respectively, i is not equal to j, $P_{Bij}$ denotes the element in the branch power outflow distribution matrix $P_B$ at an $i^{th}$ row and a $j^{th}$ column, and $P_{Bji}$ denotes the element in the branch power outflow distribution matrix $P_B$ at a $j^{th}$ row and an $i^{th}$ column.

6. The system according to claim 1, wherein an element of the power injection distribution matrix is denoted by that:

$P_{Gkj}=p$, if a $k^{th}$ generator joins up a node j and an active power flow p is injected into the node j; or $P_{Gkj}=0$, otherwise;

where, $P_{Gkj}$ denotes the element in the power injection distribution matrix $P_G$ and k is a positive integer.

7. The system according to claim 1, wherein an element of the nodal active power flow flux matrix is denoted by a formula of:

$$\begin{cases} P_{Nii} = \sum_{s \in I^+} p_{Bs} + P_{Gi} \\ P_{Nij} = 0, i \neq j \end{cases}$$

where, $I^+$ denotes a set of branches via which a power is injected into a node i, $p_{Bs}$ denotes an active power of a branch s, $P_{Nii}$ denotes the element in the nodal active power flow flux matrix $P_N$ at an $i^{th}$ row and an $i^{th}$ column, $P_{Nij}$ denotes the element in the nodal active power flow flux matrix $P_N$ at the $i^{th}$ row and an $j^{th}$ column, i and j are positive integers, and $P_{Gi}$ denotes an active output of a generator joining up the node i.

8. The system according to claim 1, wherein the nodal carbon emission flow intensities are acquired by a formula of:

$$E_N=(P_N-P_B^T)^{-1} \cdot P_G^T \cdot E_G$$

where, $E_N$ is a vector denoting the nodal carbon emission flow intensities, $P_N$ denotes the nodal active power flow flux matrix, $P_B$ denotes the branch power outflow distribution matrix, $P_G$ denotes the power injection distribution matrix and $E_G$ denotes the carbon emission intensity vector.

9. The system according to claim 1, wherein each generation carbon meter is configured to acquire the carbon emission intensity of the corresponding generator in real-time by a formula of:

$$e_G = 7 \cdot r \cdot \frac{EF_M}{q}$$

where, $e_N$ denotes the carbon emission intensity of the generator, r denotes a standard coal consumption rate for generating of the generator and is in gce/kWh, $EF_M$ denotes a carbon emission coefficient of the fossil fuel and is in kg $CO_2$/kg, q denotes a heat value of the fossil fuel and is in kcal/kg; and each generation carbon meter is further configured to display the acquired carbon emission intensity in real-time.

10. The system according to claim 9, wherein each generation carbon meter is further configured to acquire a carbon emission amount of the corresponding generator by a formula of:

$$E_{Gt}=P_{Gt} \cdot \Delta t \cdot e_{Gt};$$

and to acquire an accumulated carbon emission amount of the corresponding generator by a formula of:

$$E_G = \sum_{t \in T} P_{Gt} \cdot \Delta t \cdot e_{Gt};$$

where, $E_{Gt}$ denotes the carbon emission amount of the generator G during a period t, $E_G$ denotes the accumulated carbon emission amount of the generator G during the period t, $P_{Gt}$ denotes an active power output of the generator G during the period t, $\Delta t$ denotes a duration of the period t, $e_{Gt}$ denotes the carbon emission intensity of the generator G during the period t and T denotes a set of periods t; and each generation carbon meter is further configured to display the acquired carbon emission amount and the acquired accumulated carbon emission amount in real-time.

11. The system according to claim 1, wherein each of the transmission network carbon meters and the distribution network carbon meters is configured to acquire a carbon emission amount of a branch connecting with a node or a transformer connecting with a node by a formula of:

$$E_{Nt}=(P_{1t}-P_{2t}) \cdot \Delta t \cdot e_{Nt};$$

and to acquire an accumulated carbon emission amount of the branch connecting with the node or the transformer connecting with the node by a formula of:

$$E_N = \sum_{t \in T}(P_{1t} - P_{2t}) \cdot \Delta t \cdot e_{Nt};$$

where, $E_{Nt}$ denotes the carbon emission amount of the branch connecting with the node or the transformer connecting with the node, $E_N$ denotes the accumulated carbon emission amount of the branch connecting with the node or the transformer connecting with the node, $P_{1t}$ denotes an active power of a start node of the branch during a period t or an active power of a primary side of the transformer during a period t, $P_{2t}$ denotes an active power of an end node of the branch during the period t or an active power of a secondary side of the transformer during the period t, $e_{Nt}$ denotes a carbon emission intensity of the start node of the branch or a carbon emission intensity of the primary side of the transformer, $e_{Nt}$ is acquired from the center server, $\Delta t$ denotes a duration of the period t, and T denotes a set of periods t; and each of the transmission network carbon meters and the distribution network carbon meters is configured to display the acquired carbon emission amount and the acquired accumulated carbon emission amount in real-time.

* * * * *